(12) United States Patent
Tung et al.

(10) Patent No.: US 6,596,910 B2
(45) Date of Patent: Jul. 22, 2003

(54) PROCESS FOR THE MANUFACTURE OF FLUOROCARBONS

(75) Inventors: Hsueh Sung Tung, Getzville, NY (US); Clayton Herbert Carson, Clarence Center, NY (US); Hang Thanh Pham, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/057,570

(22) Filed: Jan. 25, 2002

(65) Prior Publication Data

US 2002/0143215 A1 Oct. 3, 2002

Related U.S. Application Data

(60) Provisional application No. 60/263,951, filed on Jan. 25, 2001.

(51) Int. Cl.⁷ .............................................. C07C 17/00
(52) U.S. Cl. ....................................................... 570/167
(58) Field of Search ......................................... 570/167

(56) References Cited

U.S. PATENT DOCUMENTS

| 5,545,773 | A | 8/1996 | Berthe ........................ 570/167 |
| 5,629,461 | A | 5/1997 | Yasuhara et al. |
| 5,714,655 | A | 2/1998 | Yamamoto et al. |
| 5,763,706 | A | 6/1998 | Tung et al. |
| 5,918,481 | A | 7/1999 | Pham et al. |
| 6,328,907 | B1 | 12/2001 | Nakada et al. |

Primary Examiner—Michael L. Shippen
(74) Attorney, Agent, or Firm—Colleen D. Szuch

(57) ABSTRACT

Disclosed is an improved HFC manufacturing processes of the type which produces an intermediate product stream that includes a mixture of HF and at least one compound, usually an HCFC, which is relatively resistant to further fluorination. The improvement involves separating the unreactive compound(s) from the product stream, preferably using liquid:liquid phase separation, and substantially avoiding recycle of the unreactive compound to the fluorination reaction. The separated unreactive compound(s) are substantially free of HF.

29 Claims, 2 Drawing Sheets

PROCESS FOR THE MANUFACTURE OF FLUOROCARBONS

This application is related to and claims the priority benefit of U.S. Provisional Patent Application No. 60/263,951, filed Jan. 25, 2001, which is incorporated herein by reference

FIELD OF THE INVENTION

The present invention relates to a process for the production of fluorocarbons.

BACKGROUND OF THE INVENTION

Hydrofluorocarbons (HFCs), i.e. compounds containing substantially only carbon, hydrogen and fluorine and no chlorine, and in particular pentafluoropropanes, are increasingly being used to replace the environmentally disadvantageous chlorofluorocarbons (CFCs) in refrigeration systems as foam blowing agents and other applications. Furthermore, it is generally commercially desirable for commercially available HFCs to be as free of hydrochlorofluorocarbons (HCFCs), i.e. compounds containing substantially only carbon, hydrogen, fluorine and chlorine, and CFCs as possible. This preference has arisen, in large part, from a widespread concern that CFCs, and to a lesser extent HCFCs, are detrimental to the Earth's ozone layer. As a result, there is a worldwide effort to use halocarbons which contain fewer chlorine atoms. In fact, some current regulations call for HFC products to contain not more than 0.5 weight percent total CFCs as an impurity, and these regulations may become more restrictive in the future. It is therefore important that certain commercial HFCs have a concentration of CFCs and HCFCS that is as low as possible.

In this regard, 1,1,1,3,3-pentafluoropropane (HFC-245fa) is considered to be a hydrofluorocarbon having zero ozone depletion potential, and is being considered as a replacement for chlorofluorocarbons in foams, refrigeration and other systems. The production of hydrofluorocarbons has been the subject of interest to provide environmentally desirable products for use as solvents, foam blowing agents, refrigerants, cleaning agents, aerosol propellants, heat transfer media, dielectrics, fire extinguishing compositions and power cycle working fluids.

It is known in the art to produce HFCs by reacting hydrogen fluoride with various hydrochlorocarbon (HCC) compounds. As is well known in the art, this type of reaction is often used in the manufacture of HFC-245fa, as is disclosed, for example, in U.S. Pat. No. 5,763,706—Tung et. al., which is assigned to the assignee of the present invention and which is incorporated herein by reference. It is common in processes involving this type of reaction to create a reaction product that contains un-reacted hydrogen fluoride, other un-reacted starting reagents, intermediate HCFC products, and the desired HFC. In such processes, a need exists to separate from the reaction product undesirable by products and un-reacted starting materials, particularly HF.

In the manufacture of certain HFCs, the reaction product is such that conventional distillation techniques can be used to separate the HF and the HFCs contained in the stream. However, certain other HFCs have a boiling point that is very close to HF and/or forms an azeotrope with HF, and the reaction product containing these HFCs can not generally be effectively and fully separated from the unwanted components using conventional distillation.

Caustic scrubbing techniques are known to be effective for separating HF from HFCs and HCFCs, even when the HFC and/or HCFC form azeotropes with HF. However, such caustic scrubbing techniques are disadvantageous because the HF which is separated from the product stream can not readily be recycled to the fluorination reaction. This lost HF tends to increase the cost of producing the desired HFC. Therefore, it is generally desirable to provide processes in which the amount of un-reacted HF recycled to the reaction step is relatively high.

A technique which has been used to separate azeotropic HFC from un-reacted HEF, while avoiding the need for caustic scrubbing, is known in the art as pressure swing distillation. See U.S. Pat. No. 5,918,481—Pham, et al., which is assigned to the assignee of the present invention and which is incorporated herein by reference. In the pressure swing distillation process, as with certain other processes that involve the separation of azeotropic HFC from un-reacted HF, a stream containing a large percentage of the un-reacted HF is produced and recycled to the fluorination reaction. In addition to the HF, however, this recycle stream also frequently includes one or more HCFCs. For many of such processes, the HCFCs that are produced are readily further fluorinated in the reaction step, and therefore including these materials in the recycle stream is generally acceptable.

Applicants have come to appreciate, however, that in other classes of such manufacturing techniques, the process produces a stream that includes one or more HCFCs that are not readily further fluorinated in the reaction step and which also form azeotropes with HF. Applicants have further recognized that this class of process, when operated according to the prior art, is characterized by an ever increasing build-up of the non-reactive HCFC in the system that needs to be purged from the system on a periodic basis. Such purging operations are disadvantageous for many reasons, including the fact that the HFC production process must normally be discontinued during the purging operation.

Applicants have come to appreciate that many of the processes currently used to produce HFC-245fa, including those which use pressure swing distillation to separate HFC-245fa from un-reacted HF, suffer from this problem of having relatively unreactive, azeotropic HCFCs in the reaction product. Applicants have discovered a process which overcomes the above-noted deficiencies in processes of this type, as explained in detail hereinafter.

SUMMARY OF TH INVENTION

Figure 1:
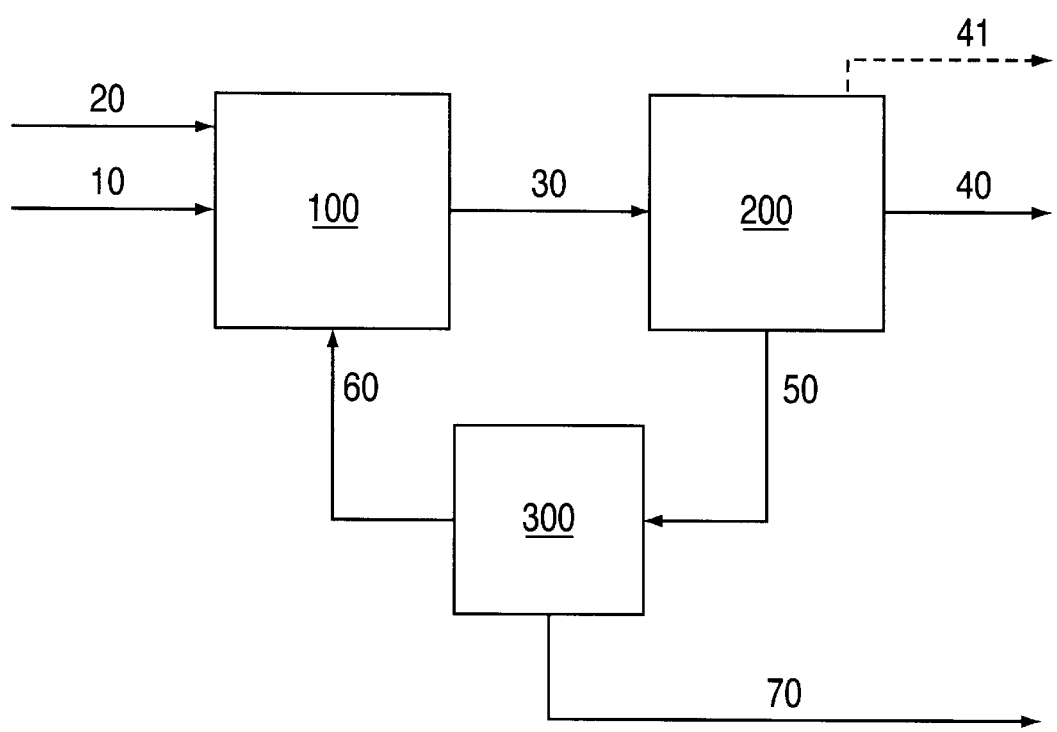
FIG. 1 is a generalized block flow diagram according to one embodiment of the present invention.

Applicants have discovered that substantial improvements can be achieved in those HFC manufacturing processes which produce a product stream that is substantially free of the desired HFC compound and which includes a mixture of HF and at least one compound, usually an HCFC, which is relatively resistant to further fluorination. As used herein, the term "relatively resistant to further fluorination" means that, under the reaction conditions used to form the desired hydrofluorocarbon, the compound is further fluorinated at a substantially lower rate (e.g., 20% lower) than the reaction rate of the primary reactant. Such compounds are also sometimes referred to herein as "unreactive" compounds. According to certain preferred embodiments, the unreactive compound is fluorinated at a rate which is at least about 40% lower, and even more preferably 60% lower, than the reaction rate of the primary reactant under the reaction conditions used to form the desired hydrofluorocarbon Applicants have discovered that processes of this type can be dramatically improved by separating unreactive compound(s) from the product stream and substantially avoiding recycle of the unreactive compounds to the fluorination reaction. According to certain embodiments of the present invention, the processes produce a product stream which includes not only un-reacted HF and relatively unreactive HCFC, but also at least one HCFC that, under the reaction conditions used in the process to form the desired HFC, is readily further fluorinated.

A compound that is considered to be "readily further fluorinated" as that term is used herein, is a compound that is fluorinated at a rate that is substantially greater than, and preferably at least about 20% greater, than the unreactive compound. Such compounds are also sometimes referred to herein as "reactive" compounds. According to certain preferred embodiments, the reactive compound is fluorinated at a rate that is not substantially less, and preferably no more than about 20% less and even more preferably no more than about 10% less, than the reaction rate of the primary reactant under the reaction conditions used to form the desired fluorocarbon. In such embodiments, the processes preferably further comprises separating said unreactive HCFC from said reactive HCFC and recycling at least a substantial portion of the reactive HCFC to said fluorination reaction.

A particular embodiment of the present invention involves a process for the manufacture of C3-HFC comprising:

a. reacting a compound selected from the group consisting of chlorinated propanes and chlorinated propenes and mixtures thereof with HF to produce a reaction product which includes at least un-reacted HF, the desired C3-HFC, an unreactive C3-HCFC, and a reactive C3-HCFC; and b. separating said reaction product into: (i) at least one product stream including a substantial portion of the desired C3-HFC in said reaction product; and (ii) at least one intermediate product stream which includes un-reacted HF, unreactive C3-HCFC, and reactive C3-HCFC;

c. separating from said intermediate product said unreactive C3-HCFC and substantially avoiding recycle of said unreactive C3-HCFC to the fluorination reaction; and d. optionally further purifying and/or recycling to the fluorination reaction the un-reacted HF and the reactive C3-HCFC in said intermediate product.

As used herein, the terms "C3-HFC" and "C3-HCFC" refer to HFCs and HCFCs, respectively, containing three carbon atoms. This embodiment of the invention is of great advantage when the C3-HFC is HFC-245fa and the reactive C3-HCFC includes HCFC-244fa (1-chloro-1,3,3,3-tetrafluoropropane) and the unreactive C3-HCFC includes HCFC-1223xd (1,2-dichloro-3,3,3-trifluoropropene). According to such embodiments, the step of separating from the intermediate product the unreactive C3-HCFC preferably comprises liquid:liquid phase separation, as described in more detail hereinafter.

The present invention is also believed to be potentially adaptable for use in the manufacture of C4-HFCs, including 1,1,1,3,3-pentafluorobutane ("HFC-365").

DETAILED DESCRIPTION OF THE INVENTION

One aspect of the present invention relates to an improved process for the manufacture of HFC which includes the step of reacting HF with one or more HFC precursors to produce a reaction product that includes the desired HFC. FIG. 1 illustrates, in a generalized block diagram form, such a process in which one or more HFC precursors, represented by feed stream 10 in FIG. 1, are introduced into a reaction step 100 together with fresh HF, represented by feed stream 20, wherein a reaction product, represented by stream 30, is produced. It is contemplated that the particulars of the reaction step in accordance with the present invention may vary greatly within the scope hereof, and accordingly all fluorination reaction particulars which are presently known or which may hereinafter be developed are adaptable for use in the present invention, provided the reaction product contains un-reacted HF and unreactive compounds, particularly and preferably unreactive compounds that form an azeotropic mixture with HF.

According to preferred embodiments in which the desired HFCs are C3-HFCs, C4-HFCs and C5-HFCs, it is generally preferred that the reaction step comprises a fluorination reaction in which HF is reacted, optionally but preferably in the presence of a fluorination catalyst, with an HFC precursor that is selected from the group consisting of Cn-HCCs, Cn-HCFCs and combinations of these, where n is 3, 4 or 5. In certain embodiments, it is preferred that the HFC precursor is selected from the group consisting of propanes and propenes, fluorinated or chlorinated, and mixtures of these. Examples of chlorinated propanes that may be used include: 1-chloro-1,3,3,3-tetrafluoropropane (HCFC-244fa); 1,1,1,3,3-pentachloropropane (HCC-240fa); trichlorodifluoropropanes (HCFC-242); 1,1-dichloro-3,3,3-trifluoropropane; and 1,3-dichloro-1,3,3-trifluoropropane, the latter two of which are each sometimes refereed to herein as HCFC-243. Examples of chlorinated propenes that may be used are 1,1,3,3-tetrachloropropene (HCC-1230za) and 1,3,3,3-tetrachloropropene (HCC-1230zd). Examples of fluorinated propenes that may be used are 1,3,3,3-tetrafluoropropene (HFC-1234ze) and 1-chloro-3,3,3-trifluoropropene (HCFC-1233zd).

For embodiments involving the manufacture of penta- or hexa-fluoropropanes, the reaction step preferably comprises one or more of the reaction steps, conditions and means that are disclosed and referred to in U.S. Pat. No. 5,763,706—Tung et. al., which is incorporated herein by reference. Under such reaction conditions, the reaction product stream will generally comprise HCl; un-reacted HF; the desired HFC, namely, HFC-245fa; HCFC-244fa; and 1,2-dichloro-3,3,3-trifluoropropene (HCFC-1223xd).

The reaction product stream 30 is processed in separation step 200 to produce at least one product stream 40 containing the desired HFC at the desired rate and in the desired purity and at least one intermediate product stream 50 that is substantially free of the desired HFC and which contains un-reacted HF and at least one unreactive compound which is difficult to separate from HF, as would occur for example when such an unreactive product forms an azeotrope with HF. According to certain embodiments, the intermediate product stream 50 also includes at least one reactive compound that is difficult to separate from the unreactive product. For example, in certain embodiments the reactive compound forms an azeotrope with HF, and the boiling point of the HF/reactive compound azeotrope is within about 10° C. of the boiling point of the HF/unreactive compound azeotrope. Stream 50 may also include other heavy boiling organic compounds produced in the reaction step. As the term is used herein, "intermediate product stream" refers to a product stream that requires further processing in accordance with the present invention.

It is contemplated that the particulars of the separation step 200 in accordance with the present invention may vary greatly within the scope hereof, and accordingly all separation processes which are presently known or which may hereinafter be developed are adaptable for use in the present invention, provided the step produces an intermediate product stream having the characteristics mentioned above with respect to stream 50. In general, the preferred separation step 200 includes the step of removing HCl, preferably substantially anhydrous HCl, from reaction product stream 30. One or more distillation columns can be used to remove anhydrous HCl from stream 30. The overhead stream from this HCl removal step is generally removed from the process, as illustrated by the dotted line 41 in FIG. 1. The remaining components are then further separated to produce at least the product stream 40 containing the desired HFC and intermediate product stream 50, preferably using conventional steps such as pressure swing distillation, as described, for example in U.S. Pat. No. 5,918,481 (which is incorporated herein by reference), or by sulfuric acid extraction, as described, for example in U.S. Pat. No. 5,895,639 (which is incorporated herein by reference), or by metal fluoride salt extraction, as described, for example in U.S. Pat. No. 5,948,381 (which is incorporated herein by reference), or by water scrubbing, or by combinations of two or more of any of these and other well known separation steps.

As mentioned above, for embodiments involving the manufacture of penta- or hexa-fluoropropanes, the preferred reaction step 100 produces a reaction product stream 30 that comprises, in addition to un-reacted HF and the desired product(s) (such as HFC-245fa), HCFC-244fa and HCFC-1223xd. The normal boiling point of HCFC-244fa is sufficiently below that of HCFC-1223xd that these two components, in a binary mixture, can be readily separated from one another by using simple distillation. More particularly, the normal boiling points of HCFC-244fa and that of HCFC-1223xd are 16° C. apart, namely, 35° C. and 51° C., respectively. However, applicants have come to appreciate that both HCFC-244fa and HCFC-1223xd not only form azeotropes with HF, thus making it difficult to separate each of these components from the HF in the reaction product, but also that the boiling points for the HCFC-1223xd/HF azeotrope and the HCFC-244fa/HF are much less than 16° C. apart. As a result, separation of the HCFC-244fa/HF azeotrope from HCFC-1223xd/HF azeotrope can not be readily achieved in the separation step 200, and therefore the stream 50, which preferably contains the un-reacted HF for recycle to the reaction step, will contain these two HCFCs.

Table 1 below reports the boiling points of these two azeotropic mixtures at several pressures. The composition of 244fa/Hf azeotrope is at about 34.7 wt % HF. The 1223xd/HF is a heterogeneous azeotrope. The 244fa/HF is a homogeneous azeotrope.

TABLE 1

| P (psia) | T° (C.) | | Δ T° (C.) |
|---|---|---|---|
| | 244fa/HF | 1223xd/HF | |
| 26.95 | 20.0 | 30.0 | 10 |
| 40.0 | 32.6 | 43.1 | 10.5 |
| 50.0 | 42.3 | 51.3 | 9 |
| 60.0 | 52.0 | 58.0 | 6 |
| 68.25 | 60.0 | 62.3 | 2 |

As can be seen from Table 1 above, the temperature differences decrease with pressure and that, due to the presence of HF in the reaction product, the boiling points of HCFC-244fa/HF and HCFC-1223xd/HF azeotropes are much closer than in the absence of HF.

The preferred embodiments of this invention include a separating step 300 for removing HF from stream 50 to produce one or more recycle streams 60 comprising a substantial portion, and preferably at least about a major proportion, of the HF present in reaction product 30. The separation step 300 preferably further comprises removing HCFC-1223xd from stream 50 to produce one or more streams 70 comprising a substantial portion, and preferably at least about a major proportion, of the HCFC-1223xd present in reaction product 30. It is contemplated that stream 70 will not be recycled to the reaction 100 but instead will be routed for further processing, sale and/or disposal.

Figure 2:
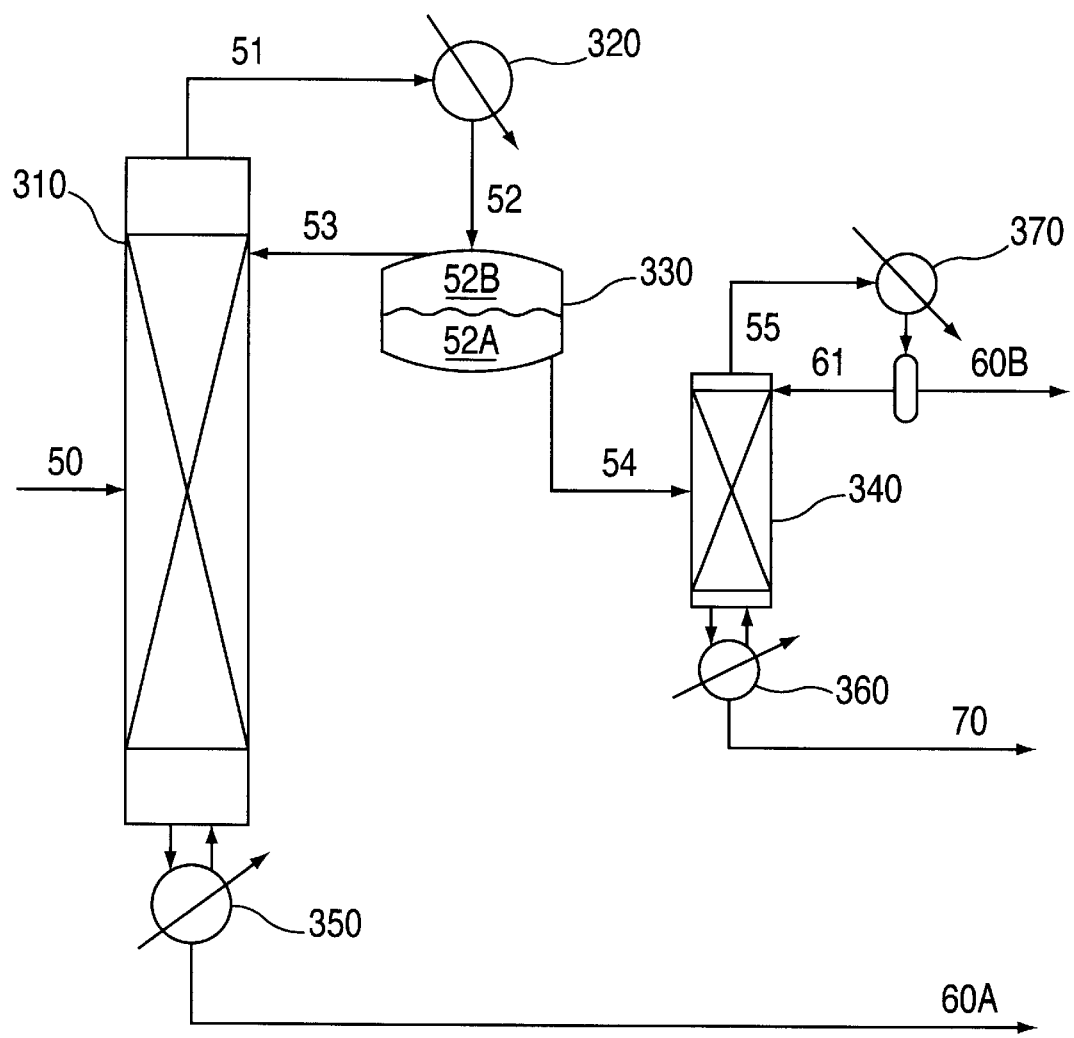
FIG. 2 is a more particularized flow diagram of one embodiment of the process of the present invention.

A preferred embodiment of the separation step 300 of the present invention is illustrated in FIG. 2. According to this embodiment, the stream 50 is introduced to a separating step 310, such as a distillation operation comprising one or more distillation towers, wherein the azeotropes of HF, together with any other organic components, are preferably removed in a vapor stream 51, which is fed to a condenser unit 320. HF which is not in an azeotropic mixture with organic compounds is removed as bottoms stream 60A, preferably after passing through reboiler 350 wherein the at least a portion of the stream is heated to the vapor state and reintroduced into the separation step 310. Stream 60A is preferably recycled to the reaction step 100.

The output stream 52 from condenser 320 comprises two liquid phases. Stream 52 is introduced into a phase separation step, such as separator drum 330, which is designed to have a volume and shape sufficient to allow stream 52 to separate into an organic phase 52A and an inorganic phase 52B. The inorganic phase is removed from the drum as stream 53 and preferably returned to distillation step 310 as reflux. The organic phase 52A is removed as stream 54 and preferably introduced into a separation step 340, such as a distillation operation comprising one or more distillation towers. The heavier organic component(s) contained in stream 54 are removed as bottoms stream 70, preferably after passing through a reboiler 360 wherein the at least a portion of the stream is heated to the vapor state and reintroduced into the separation step340. Stream 70 preferably contains the unreactive compounds contained in stream 50 and is further processed but not recycled to the reaction step, as indicated above.

The lighter organic components contained in stream 50, which preferably include the reactive compounds contained in stream 54, are preferably removed in a vapor stream 55, which is fed to a condenser unit 370. A portion of the cooled stream from the condenser 370 is introduced into the separator 340 as reflux stream 61 and the remainder of the stream is transferred to the reaction step as recycle stream 60B.

For embodiments of the present invention involving the manufacture of penta- or hexa-fluoropropanes, the stream 50 preferably includes at least about 80% by weight of the HCFC-244fa and of the HCFC-1223xd contained in the reaction product 30, together with at least a substantial portion of the un-reacted HF in the reaction product. According to highly preferred embodiments, stream 50 will comprise HCFC-244fa in an amount at least about 90% on weight basis of the HCFC-244fa in the reaction product, HCFC-1223xd in an amount at least about 90% on weight basis of the HCFC-1223xd in the reaction product, and HF in an amount at least about 90% on weight basis of the HF in the reaction product. In such embodiments, the inorganic components, which are comprised in substantial proportion of un-reacted HF, are removed in separator 310 and recycled via stream 60A to the reaction chamber 100. It is preferred that stream 60A is comprised of less than about 5% by weight of unreactive components, and particularly HCFC-1223xd, and even more preferably less than about 1% by weight of such components. Likewise, it is preferred that stream 60B is comprised of less than about 5% by weight of unreactive components, and particularly HCFC-1223-xd, and even more preferably less than about 1% by weight of such components. It is also preferred that the organic stream 54 is comprised of less than about 15% by weight of HF, more preferably less than about 10% by weight of HF and even more preferably is essentially free of HF. In separator 340, HCFC-244fa is separated from the HDCFC-1223xd by distillation, with the lower boiling HCFC-244fa being concentrated in the overhead stream 60B. It is preferred that the separator 340 is operated under conditions effective to ensure that recycle stream 60B contains less than about 5% by weight of unreactive components (such as HCFC-1223xd), and even more preferably less than about 1% by weight of such components.

Further, for embodiments of the present invention involving the manufacture of penta- or hexa-fluoropropanes, the separation step 310 is preferably operated at a pressure of from about 15 to about 200 psia, and even more preferably from about 15 to about 100 psia. The temperatures used for the separation will vary depending on the pressures used, the specific composition of stream 50, and other factors. In general, however, it is preferred that the separation operate with a bottoms temperature (e.g., reboiler input) of from about 30° C. to 100° C. and even more preferably from about 50° C. to about 70° C. and with an overhead temperature (e.g., condenser input) of from about 0° C. to 50° C. and even more preferably from about 20° C. to about 30° C. The condenser preferably operates to cool stream 51 to a temperature effective to separate the organic phase from inorganic phase. The temperature used for the condensation and phase separation step will vary depending on the pressures used, the specific composition of stream 51, and other factors. In general, however, it is preferred that stream 52 be cooled to a temperature of from about −70° C. to 5° C. and even more preferably from about −70° C. to about −20° C.

What is claimed is:

1. In a process for the preparation of a hydrofluorocarbon ("HFC") compound by the reaction of a chlorinated and/or fluorinated halocarbon with hydrogen fluoride (HF), the process being of the type which produces an intermediate product stream containing un-reacted HF, an unreactive hydrochiorofluorcarbon ("HCFC") and a reactive HCFC, the improvement comprising separating said unreactive HCFC from said intermediate product stream and substantially avoiding recycle of said unreactive HCFC to said fluorination reaction.

2. The process of claim 1 wherein said HFC is a pentafluoropropane.

3. The process of claim 1 wherein said HFC is 1,1,1,3,3-pentafluoropropane (HFC-245fa).

4. The process of claim 1 wherein said separating step comprises separating an HF-rich liquid phase from an HCFC-rich liquid phase, said HF-rich liquid phase being substantially free of at least said unreactive HCFC compound.

5. The process of claim 4 wherein at least a substantial portion of the HF in said HF-rich liquid phase is recycled to said fluorination reaction.

6. The process of claim 4 wherein said HCFC-rich liquid phase is substantially free of HF and in which at least a substantial portion of said reactive HCFC in said HCFC-rich liquid phase is recycled to said fluorination reaction.

7. The process of claim 6 wherein a substantial portion of said unreactive HCFC in said intermediate product stream is contained in said HCFC-rich liquid phase.

8. The process of claim 7 wherein substantially all of said unreactive HCFC in said intermediate product stream is contained in said HCFC-rich liquid phase and wherein no substantial portion of said unreactive HCFC in said HCFC-rich liquid phase is recycled to said fluorination reaction.

9. The process of claim 8 wherein substantially all of said unreactive HCFC in said HCFC-rich liquid phase is disposed of or further processed.

10. The process of claim 1 wherein said reactive and unreactive HCFCs each form an azeotrope with HF.

11. The process of claim 10 wherein said reactive HCFC comprises 1-chloro-1,3,3,3-tetrafluoropropane (HCFC-244fa).

12. The process of claim 11 wherein said unreactive HCFC comprises 1,2-dichloro-3,3,3-trifluoropropene (HCFC-1223xd).

13. The process of claim 12 wherein said HFC is HFC-245fa and wherein said separating step comprises separating said intermediate product stream into an HF-rich stream that is substantially free of said reactive and said unreactive HCFC and a HCFC-rich stream that contains HF and said reactive and said unreactive HCFC.

14. The process of claim 13 wherein said separating step comprises distilling said intermediate product stream into a bottom product stream comprising said HF-rich stream and a gaseous overhead stream comprising said HCFC-rich stream.

15. The process of claim 14 wherein said gaseous overhead stream is cooled to produce a stream containing a first liquid phase and a second liquid phase.

16. The process of claim 15 wherein at least a substantial portion of the HF is contained in said first liquid phase and at least a substantial portion of each of said reactive and unreactive HCFC is contained in said second liquid phase.

17. The process of claim 16 further comprising the step of separating said first liquid phase from said second liquid phase by introducing said cooled stream into a separation vessel.

18. A process for the preparation of an HFC comprising:
   a. reacting a compound with hydrogen fluoride (HF) to produce a reaction product including at least un-reacted HF, the HFC, a first fluorinated compound and a second fluorinated compound relatively more resistant to further fluorination than said first fluorinated compound; and
   b. separating said reaction product into: (i) at least one product stream including a substantial portion of the HFC contained in said reaction product; and (ii) one or more recycle steams which, in the aggregate, are substantially free of said second compound.

19. The process of claim 18 wherein said one or more recycle streams, in the aggregate, contain a substantial portion of said first compound.

20. A process for the preparation of an HFC comprising:
   a. reacting a compound with hydrogen fluoride (HF) to produce a reaction production including at least un-reacted HF, the HFC, a first fluorinated compound and a second fluorinated compound relatively more resistant to further fluorination than said first fluorinated compound, said second fluorinated compound being a compound that forms an azeotrope with HF; and b. separating said reaction product and substantially not recycling said second compound to said reacting step.

21. The process of claim 20 wherein said separating step further comprises separating said first compound from said reaction product and wherein the process further comprises recycling said separated reactive compound to said reaction step.

22. A process for the preparation of a C3-HFC comprising:
   a. reacting a compound selected from the group consisting of chlorinated propanes, chlorinated propenes, fluorinated propenes and mixtures thereof with hydrogen fluoride (HF) to produce a reaction product which includes at least un-reacted HF, the C3-HFC, a first intermediate C3-HCFC, and a second intermediate C3-HCFC that is more fluorination resistant than said first intermediate C3-HCFC; and
   b. separating said reaction product into: (i) at least one product stream including a substantial portion of the C3-HFC contained in said reaction product; and (ii) one or more recycle steams which, in the aggregate, are substantially free of said second C3-HCFC.

23. The process of claim 22 wherein said separating step comprises pressure swing distillation.

24. The process of claim 23 wherein the C3-HFC is HFC-245fa, said first intermediate C3-HCFC is HCFC 244fa, and said second intermediate C3-HCFC is HCFC-1223xd.

25. The process of claim 23 wherein said pressure swing distillation step comprises producing an intermediate product stream comprising un-reacted HF, at least a portion of said HCFC-244fa and at least portion of said HCFC-1223xd.

26. The process of claim 22 wherein said reacting step comprises a catalyzed reacting step.

27. The process of claim 1 wherein said unreactive HCFC has a fluorination rate that is at least about 20% less than the fluorination rate of said reactive HCFC.

28. The process of claim 1 wherein said unreactive HCFC has a fluorination rate that is at least about 40% less than the fluorination rate of said reactive HCFC.

29. The process of claim 1 wherein said unreactive HCFC has a fluorination rate that is at least about 60% less than the fluorination rate of said reactive HCFC.

* * * * *